US008158138B1

(12) United States Patent
Landau et al.

(10) Patent No.: US 8,158,138 B1
(45) Date of Patent: Apr. 17, 2012

(54) UREA COMPOSITIONS AND THEIR METHODS OF MANUFACTURE

(75) Inventors: Ralph Landau, Lebanon, NJ (US); Dale R. Sanson, Kansas City, MO (US); Amir Kamyar Jahani, Pensacola, FL (US)

(73) Assignee: Fougera Pharmaceuticals, Inc., Melville, NY (US)

( * ) Notice: Subject to any disclaimer, the term of this patent is extended or adjusted under 35 U.S.C. 154(b) by 397 days.

(21) Appl. No.: 10/849,531

(22) Filed: May 20, 2004

(51) Int. Cl.
*A01N 25/34* (2006.01)
*A61K 8/02* (2006.01)
*A61K 31/415* (2006.01)

(52) U.S. Cl. ......... 424/402; 424/401; 424/404; 514/399

(58) Field of Classification Search .................. 424/401, 424/402, 404; 514/399
See application file for complete search history.

(56) References Cited

U.S. PATENT DOCUMENTS

| | | | |
|---|---|---|---|
| RE29,634 E * | 5/1978 | Roberts et al. .................. 424/57 |
| 4,294,852 A | 10/1981 | Wildnauer et al. |
| 4,295,567 A | 10/1981 | Knudsen |
| 4,512,978 A | 4/1985 | Inwood |
| 4,581,351 A | 4/1986 | Berke et al. |
| 4,672,078 A | 6/1987 | Sakai et al. |
| 5,334,326 A | 8/1994 | Bostick |
| 5,340,836 A | 8/1994 | Reinhard et al. |
| 5,385,938 A | 1/1995 | Yu et al. |
| 5,407,958 A | 4/1995 | Heath et al. |
| 5,445,823 A | 8/1995 | Hall et al. |
| 5,525,635 A | 6/1996 | Moberg |
| 5,573,765 A | 11/1996 | Reinhard et al. |
| 5,632,996 A | 5/1997 | Ramirez et al. |
| 5,648,389 A | 7/1997 | Gans et al. |
| 5,707,635 A | 1/1998 | Deckner et al. |
| 5,776,920 A | 7/1998 | Quarles |
| 5,853,732 A | 12/1998 | Munden |
| 5,899,878 A | 5/1999 | Glassman |
| 5,919,470 A | 7/1999 | Valdez et al. |
| 5,968,533 A | 10/1999 | Porter et al. |
| 6,046,178 A | 4/2000 | Silvetti |
| 6,153,208 A * | 11/2000 | McAtee et al. ................ 424/402 |
| 6,262,117 B1 | 7/2001 | Sefton |
| 6,281,239 B1 * | 8/2001 | Glassman ..................... 514/399 |
| 6,380,236 B2 | 4/2002 | Glassman |
| 6,429,231 B1 | 8/2002 | Bhagwat et al. |
| 6,495,602 B1 | 12/2002 | Bhagwat et al. |
| 6,530,709 B1 | 3/2003 | Washington |
| 6,558,656 B2 | 5/2003 | Mann |
| 6,573,301 B1 | 6/2003 | Glassman et al. |
| 6,673,842 B2 | 1/2004 | Bhagwat et al. |
| 6,743,417 B2 | 6/2004 | Glassman et al. |
| 6,827,943 B2 * | 12/2004 | Glassman et al. ............ 424/401 |
| 2002/0006443 A1 | 1/2002 | Curatolo et al. |
| 2002/0155171 A1 | 10/2002 | Mann |
| 2003/0064959 A1 | 4/2003 | Sawada et al. |
| 2003/0091519 A1 | 5/2003 | Zatz et al. |
| 2003/0104080 A1 | 6/2003 | Singh et al. |
| 2003/0138466 A1 | 7/2003 | Bhagwat et al. |
| 2003/0185891 A1 | 10/2003 | Crew et al. |
| 2003/0212127 A1 | 11/2003 | Glassman et al. |
| 2004/0018221 A1 | 1/2004 | Bhagwat et al. |
| 2004/0033963 A1 | 2/2004 | Yu et al. |
| 2004/0116531 A1 * | 6/2004 | Franke et al. ................. 514/588 |
| 2004/0156870 A1 | 8/2004 | Glassman et al. |
| 2004/0156874 A1 | 8/2004 | Glassman et al. |

FOREIGN PATENT DOCUMENTS

WO  WO-96/19186  6/1996
WO  WO-98/23152  6/1998

OTHER PUBLICATIONS

Prasad et al., Antioxidant Effect of Zinc in Humans, Free Radical Biology and Medicine, 2004, vol. 37, No. 8 pp. 1182-1190.*
Bailey's Industrial Oil and Fat Products, 5th edition, vol. 5, John Wiley and Sons, Inc., pp. 358-359 and 360-379.*
Bagchi et al. (Comparative In Vitro Oxygen Radical Scavagening Ability of Zinc Methionine and Selected Zinc Salts and Antioxidants, Gen. Pharmac. vol. 28, No. 1, pp. 85-91).*
Lee and Lahti, Journal of Chemical and Engineering Data, 1972;17(3):304-306.*
"U.S. Appl. No. 11/227,102, Final Office Action mailed Mar. 10, 2009", 10 pgs.
"U.S. Appl. No. 11/202,221, Response filed Sep. 25, 2009 to Restriction Requirement mailed Feb. 2, 2009", 7 pgs.
"U.S. Appl. No. 11/202,221, Restriction Requirement mailed Feb. 2, 2009", 7 pgs.
"U.S. Appl. No. 11/227,102, Final Office Action mailed Mar. 10, 2009", 8 pgs.
"U.S. Appl. No. 11/227,102, Non-Final Office Action mailed Jul. 2, 2008", 16 pgs.
"U.S. Appl. No. 11/227,102, Response filed Jan. 2, 2009 to Non-Final Office Action mailed Jul. 2, 2008", 17 pgs.
Bailey, Alton Edward, et al., *Bailey's Industrial Oil and Fat Products*, 5th Edition, John Wiley and Sons, Inc., (1996), vol. 5: 358-359 & 360-379.
Coderch, Luisa, et al., "Ceramides and Skin Function", *American Journal of Clinical Dermatology 4(2)*, (Feb. 2003), 107-129.
Prasad, et al., "Antioxidant Effect of Zinc in Humans", *Free Radical Biology and Medicine, 37(8)*, (2004), 1182-1190.

(Continued)

Primary Examiner — San-Ming Hui
(74) *Attorney, Agent, or Firm* — Charles E. Lyon; Kristen C. Buteau; Choate, Hall & Stewart LLP

(57) ABSTRACT

Urea compositions useful for treatment of dermatological conditions. The compositions, which are free from perceptible solids, may include at least about 50 wt-% urea, zinc pyrithione, and lactic acid, and may be formulated as a topical gel.

3 Claims, No Drawings

OTHER PUBLICATIONS

"U.S. Appl. No. 11/227,102, Non-Final Office Action mailed Apr. 7, 2010", 11.

"U.S. Appl. No. 11/202,221, Non-Final Office Action mailed Mar. 24, 2010", 7 Pgs.

Groen, H., et al., "An Examination of the Crystallization of Urea from Supersaturated Aqueous and Aqueous-Methanol Solutions as Monitored In-Process Using ATR FTIR Spectroscopy", Crystal Growth & Design, 4(5), (2004), 930-936.

Haddadi, A., et al., "Preparation and characterization of biodegradable urea-loaded microparticles as an approach for transdermal delivery", J Microencapsul., 23(6), (Sep. 2006), 698-712.

Sorell, L. S, et al., "Diffusivity of urea in concentrated, saturated and supersaturated solutions", AIChE Journal, 28(5), (1982), 772-779.

Thomas, R., Definition of the term "gel" (from Stedman's Medical Dictionary, Copyright, (2002-2010)).

"U.S. Appl. No. 11/202,221, Response filed Sep. 24, 2010 to Non Final Office Action mailed Mar. 24, 2010", 8 pgs.

"U.S. Appl. No. 11/202,221, Response filed Dec. 30, 2010 to Final Office Action mailed Nov. 5, 2010", 10 pgs.

"U.S. Appl. No. 11/227,102, Final Office Action mailed Dec. 15, 2010", 8 pgs.

"U.S. Appl. No. 11/227,102, Response filed Oct. 7, 2010 to Non Final Office Action mailed Apr. 7, 2010", 18 pgs.

"U.S. Appl. No. 11/227,102, Response filed Nov. 2, 2009 to Final Office Action mailed Mar. 10, 2009", 17 pgs.

"U.S. Appl. No. 11/202,221 Final Office Action mailed Nov. 5, 2010", 7 pgs.

Allerderm Laboratories, U-Lactin Lotion, at http://www.allerderm.com/consumers/ulactin.asp (Apr. 8, 2004).

Doak Dermatologics, Carmol 40Rx Lotion, Carmol40Rx Cream, Carmol40Rx Gel product label, 2002.

Friedman-Birnbaum, R. et al., "Treatment of onychomycosis: A randomized, double-blind comparison study with topical bifonazole-urea ointment alone and in combination with short-duration oral griseofulvin," International Journal of Dermatology, 36(1): 67-69 (1997) (Abstract).

Gennaro et al., editors, Remington's Pharmaceutical Sciences, 18th ed., 767-768 and 1329 (1990).

Gennaro, Remington's Pharmaceutical Science, 18th ed., pp. 1305, 1310, 1317 and 1329 (1990).

Gloor, M. et al., "Do Urea/Ammonium Lactate Combinations Achieve Better Skin Protection and Hydration than Either Component Alone?," Skin Pharmacol. Appl. Skin Physiol., 15:35-43 (2002).

Laboratoires SVR, Xerial 50, product label, 2004.

Lucy, J.A., "Functional and Structural Aspects of Biological Membranes: A Suggested Structural Role for Vitamin E in the Control of Membrane Permeability and Stability," Annals of the New York Academy of Sciences, 203: 4-11 (Dec. 18, 1972).

Scharffetter-Kochanek, K. et al., "Photoaging of the skin from phenotype to mechanisms," Experimental Gerontoloty, 35(3): 307-316 (May 2000).

Thiele, J.J., "The Antioxidant Network of the Stratum corneum," Curr. Probl Dermatol., 29: 26-42 (2001).

\* cited by examiner

UREA COMPOSITIONS AND THEIR METHODS OF MANUFACTURE

BACKGROUND OF THE INVENTION

1. Field of the Invention

The present invention is directed to dermatological compositions. More particularly, the present invention is directed to urea compositions, methods of making urea compositions, and methods of using urea compositions to treat dermatological conditions.

2. Related Art

Urea is recognized as a cosmetic ingredient in formulations, typically acting as a humectant or a moisturizer. Urea is also recognized as a medically useful keratolytic agent because of urea's ability at high concentrations to solubilize and denature protein. For example, U.S. Pat. No. 5,919,470 describes dermatological compositions using concentrations of urea of about 21 to about 40 wt-% for treating xerosis and other skin conditions. Topical compositions of about 40 wt-% urea are available (for example, Carmol®40Rx, available from Doak Dermatologics, Fairfield, N.J.). Such compositions are useful for the treatment of various dermatological conditions, such as onychomycosis, as described in, for example, the following U.S. Pat. Nos. 6,281,239; 6,380,236; 6,429,231; and 6,673,842.

Such known compositions typically have a maximum concentration of urea of about 40 wt-%. This is because of the difficulty in dissolving or solubilizing all of the urea at concentrations above about 40 wt-%. At concentrations above about 40 wt-%, the urea cannot be fully dissolved in the aqueous medium or emulsion, resulting in precipitation of the excess urea. Precipitation becomes particularly acute when high concentrations of urea are dissolved at elevated temperatures (70-80° C.) at which the urea is more soluble, and then the mixture is cooled to room temperature range (20-25° C.). During the cooling process, the urea precipitates in the form of needles of urea (a crystalline phenomenon well known in chemistry), which result in a non-smooth gritty feel to the final product. Such a gritty feel resulting from concentrations of urea greater than 40% is exemplified by the Xerial 50 product, available from Laboratories SVR, Bondoufle, France (this product is labeled at 50% urea). Products having such a gritty feel are not ideal dermatological products—they are not absorbed into the skin quickly, and they can be painful when applied to any type of compromised skin.

There is thus a need in the art for methods of preparing urea compositions having a urea concentration above about 40 wt-% that are smooth and non-gritty. There is also a need in the art for such urea compositions. There is also a need in the art for urea compositions that incorporate other dermatologically useful components into a single composition. The present invention provides such methods and compositions.

SUMMARY OF THE INVENTION

The present invention is directed to urea compositions, methods of making urea compositions, and methods of treating dermatological conditions using urea compositions. In a first aspect of the present invention, a urea composition is provided that comprises from about 21 to about 60 wt-% urea, a trace metal (zinc, copper, manganese) compound, a lipid, and, an antioxidant. Such urea compositions are preferably formulated as a cream or a lotion that are semi-solid at room temperature. The trace metal compound may be a zinc compound, such as zinc pyrithione. The lipid component may include one or more of a ceramide, a caprylic and or capric triglyceride, linoleic acid, any omega 6 fatty acid, and cholesterol. The antioxidant may include a tocopherol, such as Vitamin E, Vitamin A, and Vitamin C.

In another aspect of the present invention, a urea composition is provided that comprises at least about 50 wt-% urea, and a trace metal (zinc, copper, manganese) compound. Such urea compositions are preferably formulated as a cream that is semi-solid at room temperature, or as a gel that is liquid at room temperature. The trace metal compound may be a zinc compound, such as zinc pyrithione. The gel formulation may include propylene glycol, and may be free from glycerin. The gel formulation also may include lactic acid.

In yet another aspect of the present invention, a urea composition is provided that comprises about 35 wt-% urea, about 2.0 wt-% lactic acid, and one or more thickeners sufficient to provide a viscosity in the range of about 15000 to about 30000 centipoise at 25° C. In another aspect of the present invention, a urea composition is provided that comprises about 50 wt-% urea, about 2.0 wt-% lactic acid, and one or more thickeners sufficient to provide a viscosity of about 70000 centipoise at 25° C.

In another aspect of the present invention, a method for making a urea composition is provided. Such a method comprises:

combining a first phase and a second phase to form a combined phase, wherein the first phase comprises a first portion of urea and the second phase comprises a lipid and an antioxidant;

cooling the combined phase to form a cooled combined phase; and after the cooling step, adding a second portion of urea to the cooled combined phase to form a mixture.

In yet another aspect of the present invention, another method for making a urea composition is provided. Such a method comprises:

combining a first phase and a second phase to form a combined phase, wherein the first phase comprises a first portion of urea and the second phase comprises propylene glycol and xanthan gum;

adding a second portion of urea to the combined phase to form a mixture; and processing the mixture through a colloid mill.

The above methods described in the two previous paragraphs may also include prior to the adding step, grinding or milling the second portion of the urea. Such a method may also include after the adding step, processing the mixture through a colloid mill. Each milling operation provides control of the particle size, which is important to the ultimate feel, and therefore viability, of the resulting product.

In another aspect of the present invention, another method for making a urea composition is provided. Such a method comprises:

mixing water, a carbomer, and urea to form an aqueous phase;

heating to a temperature of approximately 70-80° C. a lipid and an antioxidant to form a heated organic phase;

combining the aqueous phase and the heated organic phase to form a heated combined phase;

cooling the heated combined phase to a temperature of about 20-25° C. in about one hour to form a cooled combined phase; and adding a trace metal compound to the cooled combined phase to form a mixture, wherein the trace metal is selected from the group consisting of zinc, copper, and manganese.

In yet another aspect of the present invention, a further method for making a urea composition is provided. Such a method comprises:

combining a first phase and a second phase to form a combined phase, wherein the first phase comprises a first portion of urea and the second phase comprises a second portion of urea, propylene glycol and xanthan gum;

adding a trace metal compound to the combined phase to form a mixture, wherein the trace metal is selected from the group consisting of zinc, copper, and manganese; and processing the mixture through a colloid mill.

Such a method may also include prior to the adding step, milling the second portion of the urea.

In yet a further aspect of the present invention, a method for making a urea composition that comprises a quantity of urea is provided. Such a method comprises:

combining a first phase and a second phase to form a combined phase, wherein the first phase comprises the quantity of urea and the second phase comprises a lipid and an antioxidant;

cooling the combined phase to form a cooled combined phase;

after the cooling step, adding a trace metal compound to the cooled combined phase to form a mixture, wherein the trace metal is selected from the group consisting of zinc, copper, and manganese; and processing the mixture through a colloid mill.

In yet a further aspect of the present invention, another method for making a urea composition that comprises a quantity of urea is provided. Such a method comprises:

combining a first phase and a second phase to form a combined phase, wherein the first phase comprises the quantity of urea and the second phase comprises propylene glycol and xanthan gum;

adding a trace metal compound to the combined phase to form a mixture, wherein the trace metal is selected from the group consisting of zinc, copper, and manganese; and processing the mixture through a colloid mill.

The above methods described in the two previous paragraphs may also include carrying out the processing step until the composition is free from perceptible solids. The processing step may be carried out, for example, using one or more colloid mills.

In yet further aspects of the present invention, the urea compositions are used to treat dermatological conditions.

The present invention advantageously provides urea compositions having a urea concentration above about 40 wt-% that are smooth and non-gritty.

The compositions of the present invention advantageously combine into a single composition the therapeutic benefits of urea, trace metals, lipids, and antioxidants.

The compositions of the present invention also advantageously provide the benefit of urea concentrations of about 50 wt-% in compositions formulated as a cream or as a gel.

In one aspect of the present invention, a urea cream topical product is provided that incorporates lactic acid. Such a topical product advantageously has a slightly acidic pH (a pH of approximately 6), which is ideal for the skin. Urea-only topical products typically have a pH greater than 7, which is not ideal for the skin. All of the products of the present invention may have a slightly acidic pH, for example, a pH of approximately 6 or less.

The present invention advantageously provides compositions that are free from preservatives. In addition to all its dermatological benefits, urea conveys an anti-microbial property to a sufficient extent such that preservatives are not required.

The methods of the present invention advantageously provide manufacturing processes that result in a composition that contains a high level of urea, and that has a smooth, non-gritty feel, free from the feel or perception of any solids. The methods of the present invention advantageously provide novel methods for reducing the precipitation of urea crystals during the preparation of urea formulations having a concentration greater than about 40 wt-%.

The present invention advantageously provides compositions suitable for treating a number of dermatological conditions, including, for example, onychomycosis, xerosis, icthyosis, psoriasis, and atopic dermatitis.

DETAILED DESCRIPTION OF THE PREFERRED EMBODIMENTS

Overview

The present invention is directed toward compositions containing urea, and methods for making such compositions. The present invention is also directed to methods of using urea compositions to treat dermatological conditions. The urea compositions of the present invention are preferably used for the treatment of dermatological conditions generally manifested by thick, rough dry skin and/or hardened, discolored, diseased, damaged, devitalized nails and cutaneous wounds. The compositions of the present invention can also be advantageously used for the treatment of dry skin clinically characterized as xerosis, and for the temporary relief of symptoms associated with various pathological dermatological conditions, including, for example, ichthyosis, psoriasis and atopic dermatitis.

The compositions of the present invention can be formulated for topical application as a cream, a lotion, or a gel. One composition of the present invention comprises from about 21 to about 60 wt-% urea, a zinc, copper or manganese trace metal compound, a lipid, and an antioxidant. Another composition of the present invention comprises at least 50 wt-% urea and a zinc, copper or manganese trace metal compound. In preferred embodiments of the present invention, the trace metal compound is zinc pyrithione, the lipid component includes one or more of a ceramide, a caprylic and/or capric triglyceride, linoleic acid, and cholesterol, and the antioxidant is vitamin E.

The present invention is also directed to methods for making urea compositions, particularly urea compositions that comprise at least about 50 wt-% urea. For compositions that comprise at least about 50 wt-% urea, conventional manufacturing processes are unsuitable because the urea is present in the composition above its solubility limit, resulting in urea crystal formation and a gritty product not suitable for dermatological applications. To solve the problems associated with the high concentration of urea in the composition, the methods of the present invention were developed to obtain a composition that contains a high level of urea, and that has a smooth, non-gritty feel, free from the feel or perception of any solids. The challenge is to eliminate, to the extent possible, all crystals, and to minimize agglomeration, which can also generate a feeling of "grittiness."

As will be explained in more detail below, the methods of the present invention reduce and/or eliminate crystallization of the supersaturated urea, thereby reducing crystal formation. A number of inventive methods were developed to reduce crystallization and agglomeration of the urea. In one aspect, hydroxyethylcellulose and xanthan gum are added along with moderate blending to incorporate air into the mixture. The air in the mixture appears to act as a barrier to prevent the supersaturated urea from crystallizing. The air pockets prevent many of the urea particles from encountering each other, thereby reducing coalescence (agglomeration) and crystal growth.

In another aspect of the present application, crystal growth is reduced through the addition of urea in two steps. The second addition of urea is a significant advance in the art in that it provides a mechanism for elimination of the "gritty" feel in urea products having a high concentration of urea. A first portion of the urea is added to a first, aqueous phase. The aqueous phase is combined with a second, organic phase, mixed at an elevated temperature, and then cooled. A second or remaining portion of the urea is then added to the combined aqueous and organic phases. The first portion of the urea is dissolved in the aqueous phase, and remains in the continuous aqueous phase after the emulsion is formed (when the aqueous and organic phases are combined). The second portion of the urea is incorporated physically into the emulsion, but is not dissolved like the initial or first portion of urea. The two-step urea addition process of the present invention is preferably carried out so that upon cooling of the emulsion (formed by the combined aqueous and organic phases), none of the first portion of the urea precipitates. If the urea does not precipitate, it will not form crystals. Moreover, by controlling the particle size of the second portion of the urea, and by adding the urea to the emulsion in a manner that minimizes agglomeration, a product may be produced that has no perceptible solids.

To provide a smooth, non-gritty texture to the final product, the second portion of the urea may be formed by grinding or milling dry solid urea. By grinding or milling is meant an action to reduce a particle size of a solid. The present invention may be carried out using any particle-size reducing apparatus that operates on solid particles to reduce their size. One suitable apparatus is a mill, such as, for example, a Fitz mill, an ACM or air classifying mill, a Mikro-Pulverizer, an air mill or a hammer mill. In one embodiment of the present invention, the second portion of the urea is milled so that the particles have a mean particle size less than about 200 microns (t), alternatively less than about 150 microns, and alternatively less than about 75 microns. In another embodiment of the present invention, 75 wt-% of the particles in the second portion of the urea have a mean particle size in the range of from about 50 to about 150 microns, and the remaining 25 wt-% of the particles in the second portion of the urea have a mean particle size greater than about 150 microns. In one embodiment of the present invention, an ACM is used to mill the second portion of the urea so that approximately 85 wt-% of the urea in the second portion has a particle size less than 150 microns, and approximately 79 wt % of the urea in the second portion has a particle size less than 75 microns. In one embodiment of the present invention, the second portion of urea has a particle size distribution as shown below in Table 1. The particle size distribution shown in Table 1 was determined by the wet sieve method using 25 grams of dry solid urea milled using an ACM. As shown in Table 1 seven trays were used, the top tray having an 850 micron opening (mesh size 20), with the bottom tray having no opening (no mesh—referred to below as "pan"). The 25 gram sample of urea was placed in the top tray, and the tower of trays was vibrated so that the urea particles would fall through the mesh in the trays until they reached the tray having an opening (mesh size) too small to fall through. For example, 80 micron urea particles would fall through the tower until reaching the tray having the 75 micron opening in the mesh where they would be stopped from falling through. The urea particles were collected from each tray, and the wt-% calculated. As can be seen below in Table 1, 79.00 wt-% of the particles fell all the way through to the bottom (no mesh), and 5.96 wt-% of the particles stopped at the 75 micron tray (and thus have a particles size less than 150 microns and greater than 75 microns). Table 1 shows that approximately 85 wt-% of the particles have a size less than 150 microns, and that greater than 50 wt-% of the particles have a size less than 75 microns.

TABLE 1

| Net Weight (grams) | Weight % | Mesh Opening (μ) | Mesh Size |
|---|---|---|---|
| 0.29 | 1.16 | 850 | 20 |
| 1.67 | 6.68 | 425 | 40 |
| 1.10 | 4.40 | 250 | 60 |
| 0.44 | 1.76 | 180 | 80 |
| 0.26 | 1.04 | 150 | 100 |
| 1.49 | 5.96 | 75 | 200 |
| 19.75 | 79.00 | 0 | Pan |
| Total: 25.00 | Total: 100.00 | | |

Milling the second portion of the urea as described above makes it like talcum powder at the time of its addition to the emulsion. By adding the second portion of the urea to the emulsion in a manner that minimizes agglomeration, a product may be produced that has no perceptible solids, In particular, the second portion of the urea is preferably added to the emulsion in a uniform, well spread manner. This can be achieved, for example, by uniformly spreading the second portion of urea on a screen through which the urea passes into the emulsion. Alternatively, a conveyor could be used to dispense the milled urea in a continuous fashion, much like the addition of sifted flour into a sauce. Use of a screen or other like apparatus to minimize agglomeration of the second portion of the urea as it is added to the emulsion is another factor that improves the smooth, creamy feel of the final product.

The mixture resulting from the addition of the second portion of the urea to the emulsion may then be run through a colloid mill to reduce any agglomerates, thereby providing a final composition having a smooth, creamy, non-gritty feel. The colloid mill reduces the size of any particulates, including solids and emulsion droplets or agglomerates, that are larger than the minimum gap set in the colloid mill, such as, for example, the hammer gap in a hammer colloid mill.

In an alternate embodiment of the present invention, both the first and the second portions of the urea may be milled to a mean particle size less than about 200 microns alternatively less than about 150 microns, and alternatively less than about 75 microns. In such an alternative embodiment as well, the first portion of the urea is dissolved in the first phase, and the second portion of the urea is added to the emulsion in a talcum powder like form.

In yet another embodiment of the present invention, all of the urea may be added to the aqueous phase, which is then combined with the organic phase to produce the emulsion. In such an embodiment, all of the urea may optionally be milled to have a mean particle size less than about 200 microns, alternatively less than about 150 microns, and alternatively less than about 75 microns. The final composition is then run through one or more colloid mills to break up the crystallized urea and agglomerates to produce a product without a perceptible gritty feel.

In an embodiment of the present invention, the composition comprises about 50 wt-% urea. In such an embodiment, the first portion of urea is about 35 wt-% and the second portion is about 15 wt-%. In another embodiment of the present invention, the first portion of urea may be about 60 to about 70 wt-% of the urea present in the composition, and the second portion of urea may be about 40 to about 30 wt-% of the urea present in the composition.

For gel formulations of the present invention, it has been discovered that propylene glycol appears to act in much the same way in the gel as incorporation of air into the cream to reduce crystallization of the urea. The glycol molecules appear to hinder the urea molecules from encountering each other in the formulation, thereby reducing the amount of urea crystal growth. Moreover, it has been discovered that a viscosity in the range of about 5000 to about 50000 centipoise (measured at 25° C.), and, in particular, a viscosity in the range of about 10000 to about 20000 centipoise (measured at 25° C.) is optimal to incorporate and retain at least about 50 wt-% urea in a gel composition.

Compositions of the Present Invention

The present invention is directed toward urea compositions. Urea is recognized as a cosmetic ingredient in formulations, typically acting as a humectant or a moisturizer. Urea is also recognized as a medically useful keratolytic agent because of urea's ability at high concentrations to solubilize and denature protein. Urea has antimicrobial properties, is known to have a strong proteolytic action, and is an effective keratolytic agent particularly in the range of 30 to 60 wt-%. Urea is very effective in dispersing epidermal keratin. Urea has the unique property of binding water and thereby allows the stratum corneum of the skin to retain water resulting in relief from dry skin disorders. Urea is non-toxic even at these high concentrations. Urea is an excellent chemical debridement agent, particularly for eschar and devitalized skin and nail disorders and can be applied directly to the wound because it is non-toxic.

Although retention of water in the stratum corneum is essential to relieve dry skin conditions, this is not the only factor for healthy skin. Stratum corneum lipids (oil/organic molecules) are important components of the epidermal permeability barrier. Lipids are responsible for providing a barrier effect against the loss of moisture and provide protection from other types of external elements or "aggressions." In the superficial stratum corneum, these lipids are primarily composed of ceramides.

Ceramides are a natural part of the cell membrane in the outermost layer of the epidermis. Ceramides consist of a long-chain or sphingoid base linked to a fatty acid via an amide bond. Ceramides are formed as the key intermediates in the biosynthesis of all the complex sphingolipids, in which the terminal primary hydroxyl group is linked to carbohydrate, phosphate, etc. The stratum corneum of the skin in which the outer-most layer consists of dead cells contains relatively high levels of distinctive ceramides, including O-acylceramides, together with free fatty acids and cholesterol. Some of these skin ceramides have distinctive structures not seen in other tissues. They can contain the normal range of longer-chain fatty acids (some with hydroxyl groups in position 2), linked both to dihydroxy bases with trans-double bonds in position 4 or to trihydroxy bases. In addition, there are O-acyl ceramides in which the long-chain fatty acid component (typically $C_{30}$) has a terminal hydroxyl group, which may be in the free form or esterified with either linoleic acid or a 2-hydroxy acid. The sphingoid base can be either a di- or trihydroxy base. In addition, the omega-hydroxy-ceramides may occur covalently bound to proteins in certain skin cells. Ceramides are critical in helping the skin to maintain its moisture-binding and protective barrier functions. Since ceramides make up 40% of the lipid component of the intercellular matrix, which binds epidermal skin cells together, they play a key role in maintaining the moisture level and suppleness of the skin. A chronic decline of the ceramide concentration in the skin's intercellular matrix has been demonstrated to be part of the skin aging process; its loss allows for penetration of damaging environmental elements and results in trans epidermal evaporation of moisture. Skin xerosis, particularly associated with aging, results from decreases in dermal and stratum corneum ceramide content. The other lipophilic components described herein also benefit from this relationship, thus providing an effective product to alleviate dry skin and other dermatological conditions. The compositions disclosed in this invention include ceramides as part of the lipid component along with other natural lipids, including, for example, caprylic and or capric triglycerides, linoleic acid, and cholesterol. Caprylic/capric triglycerides are natural lipids and have excellent skin protecting, conditioning and moisturizing properties. Caprylic/capric triglycerides are hydrolyzed to short chain fatty acids (caprylic acid and capric acid).

As would be readily apparent to one skilled in the art, the present invention is not limited to the foregoing lipid components, and other natural and or synthetic lipid components can be used. Suitable lipids include any organic dermatologically acceptable organic phase excipient.

Linoleic acid is a naturally occurring omega-6 fatty acid. Linoleic acid is the most important of the three essential fatty acids. The other two (linolenic and arachidonic) can be manufactured from linoleic acid. Linoleic acid is vital for the health of the skin and mucous membranes. It aids in oxygen transport and cellular respiration. It protects the skin from sunlight, and stimulates the growth of new cells. Cholesterol is a natural lipid in the body. Cholesterol promotes adhesion of skin cells and acts as an excellent moisturizer.

Damage to skin from environmental factors is another skin health area that an ideal topical dermatological product addresses. Of the various environmental factors, probably the most damaging is from the effects of oxidation and free radicals. Free radicals are highly reactive molecules that bind to and destroy compounds in tissue cells. Most free radicals in the human body are produced in the body, while others come from the environment and foods.

One antioxidant, vitamin E, is of particular interest. The term "vitamin E" includes tocopherol (vitamin E) and derivatives thereof such as, for example, $\alpha$-, $\beta$-, $\gamma$-, $\delta$-, $\epsilon$-, $\zeta_1$, $\zeta_2$, and $\eta$-tocopherol, and $\alpha$-tocopherol acid succinate. Vitamin E is known as an antioxidant and protective vitamin for phospholipids of the cell membrane. It maintains the permeability and stability of the cell membrane, *Lucy. Annals N.Y. Academy of Science* 203, p. 4 (1972). It further has been known that vitamin E has a membrane-sealing effect. In erythrocytes, the simplest cells of the human body, it has been found that vitamin E provides a protective effect for the cell membrane. As with all antioxidants, vitamin E protects cells including, epidermal cells, which are susceptible to a wide range of oxidating events. Vitamin E has excellent antioxidant properties. It prevents the enzymatic action of peroxidases on unsaturated bonds in the cell membrane. It also has the ability to neutralize free radicals, which are naturally occurring unstable molecules that can cause great damage to skin and tissue.

Antioxidants include, but are not limited to, tocopherols (vitamin E), tocopherol derivatives, tocotrienols, ascorbic acid (vitamin C), ascorbic acid derivatives, carotenoids, vitamin A or derivatives thereof, butylated hydroxytoluene, butylated hydroxyanisole, gallic esters, flavonoids such as, for example, quercetin or myricetin, selenium, grape seed extract, catechins such as, for example, epicatechin, epicatechingallate, epigallocatechin or epigallocatechingallate, sulfur-containing molecules such as, for example, glutathione, cysteine, lipoic acid, N-acetylcysteine, chelating agents such as, for example, ethylenediamine tetraacetic acid or other customary antioxidants.

Trace elements play an important role in the biochemistry of living organisms including wound healing and healthy skin. Trace amounts of zinc, copper and manganese are known to help in accelerating the healing of cutaneous wounds. Although the mechanism by which this is achieved is not clearly understood, these trace elements accelerate the re-epithelialization of cutaneous wounds. Zinc, copper and manganese promote keratinocyte proliferation. The present invention may contain a trace metal compound of zinc, copper or manganese, such as, for example, a biocompatible salt or complex of zinc, copper, or manganese. In a preferred embodiment of the present invention, the composition includes zinc pyrithione as the trace metal compound. Zinc pyrithione also has antimicrobial properties. In other embodiments of the present invention, other trace metal compounds may be used. For example, the present invention may include biocompatible salts of manganese such as manganese carbonate, chloride, gluconate, glycerophosphate, lactate, or nitrate. Examples of copper biocompatible salts include, but are not limited to, copper acetate, bromide, carbonate, chloride, citrate, gluconate, glycinate, iodide or nitrate. Biocompatible zinc salts include, but are not limited to, zinc acetate, bromide, carbonate, chloride, citrate, gluconate, glycinate, lactate, nitrate, or sulfate. In one embodiment, gluconate salts are used that are commercially available, for example, from Spectrum Chemical and Laboratory Products, Gardena, Calif.

Lactic acid, an α-hydroxy acid, is reported to be one of the most effective naturally occurring humectants in the skin. The α-hydroxy acids (and their salts), in addition to having beneficial effects on dry skin, have also been shown to reduce excessive epidermal keratinization in patients with hyperkeratotic conditions (e.g., ichthyosis). In one embodiment of the present invention, lactic acid is included in the compositions.

The compositions of the present invention may contain urea, lactic acid, both natural humectant and moisturizers, combined with natural lipid components like ceramides, caprylic/capric triglycerides, linoleic acid, cholesterol and antioxidants. Zinc pyrithione provides trace metals, which are included for wound healing properties as they accelerate the re-epithelialization of cutaneous wounds. These novel combinations of natural ingredients together provide a unique dermatological therapy for treating a variety of dermatological conditions generally manifested by thick, rough dry skin and/or hardened, discolored, diseased, damaged, devitalized nails.

One composition of the present invention comprises from about 21 to about 60 wt-% urea, a zinc, copper or manganese trace metal compound, a lipid, and an antioxidant. Another composition of the present invention comprises at least 50 wt-% urea and a zinc, copper or manganese trace metal compound. Antibacterial properties of the urea allow the composition of the present invention to be free of conventional preservatives such as methyl paraben, propyl and butyl imidazolidinylurea, diazolidinylurea, methylchloroisothiazolinone and methylisothiazolinone.

The compositions of the present invention also preferably contain dermatologically acceptable excipients, such as for example emulsifiers and thickeners. Among these are, for example, C16 to C18 straight or branched chain fatty alcohols or fatty acids, or mixtures thereof. Preferably these include cetyl alcohol, stearyl alcohol, stearic acid, palmitic acid, or mixtures thereof. Fatty acids or fatty alcohols may be present from about 0.25 to 3 wt-%.

Xanthan gum is another ingredient that may be used in the present invention. Xanthan gum is a high molecular weight heteropolysaccharide gum produced by pure-culture fermentation of a carbohydrate with xanthomonas campestris (CP Kelco). The gum is also commercially available from various sources, including Rhone-Poulenc (Rhodigel or Rhodopol).

As part of the dermatologically acceptable excipients, the composition includes thickeners that provide a high viscosity cream, lotion or gel designed to remain in place upon application to the skin. Preferred thickeners include a mixture of a carbomer and triethanolamine. The mixture is combined together and added to the composition in an amount totaling anywhere from about 0.05 to 5 wt-%. Triethanolamine is available as Trolamine NF from BASF. The carbomers come in various molecular weights and identified by numbers. These are otherwise known as carbopol. One carbomer suitable for use with the present invention is Carbopol 940. Carbomers are homopolymers of acrylic acid crosslinked with an allyl ether of pentaerytritol, an allyl ether of sucrose or an allyl ether of propylene. The carbomer is used in the composition of the present invention as a thickener, but it is also used to suspend and stabilize the emulsion. Although Carbopol 940 is preferably used in the present invention, other analogs may also be used such as carbomer 910, 2984, 5984, 954, 980, 981, 941 and 934. Carbopol ETD 2001, 2020, and 2050 and Ultrez 20 are also commercially available and suitable for use with the present invention.

The following examples are provided to illustrate the compositions and methods of the present invention. As would be understood by one skilled in the art, the present invention is not limited by the following examples, and includes the use of other ingredients and percentages.

Example 1

50 wt-% Urea Cream

| Ingredients | Mass (gms) | Wt-% |
| --- | --- | --- |
| 1) Purified water | 302.25 | 30.23% |
| 2) Edetate disodium | 1 | 0.10% |
| 3) Cosmedia | 3 | 0.30% |
| 4) Carbomer | 1.75 | 0.18% |
| 5) Hydroxyethylcellulose | 0.5 | 0.05% |
| 6) Urea | 503 | 50.30% |
| 7) Xanthan gum | 0.5 | 0.05% |
| 8) Carprylic triglycerides | 50 | 5.00% |
| 9) Ceramides | 1 | 0.10% |
| 10) Linoleic acid | 7.5 | 0.75% |
| 11) Cholesterol | 8 | 0.80% |
| 12) Span 60 | 7.5 | 0.75% |
| 13) Tween 60 | 15 | 1.50% |
| 14) Cetyl alcohol | 13 | 1.30% |
| 15) Vitamin E | 30 | 3.00% |
| 16) Trolamine | 35 | 3.50% |
| 17) Lactic acid | 20 | 2.00% |
| 18) Zinc pyrithione | 1 | 0.10% |
| Sum = | 1000 | 100.00% |

To prepare the aqueous phase, the purified water was added to a water jacketed reactor preheated to 75° C. Then the edetate disodium was added, and mixed for 5 minutes. Suitable mixers for the aqueous phase include, but are not limited to, a side sweep mixer, turbine mixer, and high shear homogenizer. The Cosmedia (cosmetic base for emulsion, available from Stepan Inc., Northfield, Ill.) was added, and the combination was mixed for an additional 5 minutes. The hydroxyethylcellulose (Aqualon/Hercules) was added, and mixed for 10 minutes to allow proper swelling. The xanthan gum (CP Kelco) was added after the hydroxyethylcellulose, and the mixture was mixed for another 5 minutes. The carbomer (Carbopol 940) was added, and the mixture was mixed for 10-15 minutes. Finally, 5.0 grams of Tween 60 and the first portion of the urea (Urea USP, Chemische Fabrik Lehrte), 303 grams, were added. The 303 grams of urea added to the aqueous phase constitutes about 60 wt-% of the 503 grams of urea present in the final composition. The mixing accompanying the addition of the hydroxyethylcellulose and the xanthan gum incorporates air into the mixture, thereby providing a barrier that reduces the crystallization of the supersaturated urea in the cream. Reduction of the crystallization of the urea provides a cream composition that has a smooth, whipped consistency.

To prepare the organic phase, ingredients 8) through 12) (Span 60 is an emulsifier, sorbitan monostearate), 10.0 grams of Tween 60, and ingredients 14), 15), and 17) were combined in a separate container and heated to approximately 70° C. until visually homogenous (10-15 minutes). The organic phase was added to the aqueous phase, and mixed for 15 minutes at 70° C. The mixture was cooled to 15-20° C. over the course of one hour. The remaining urea (second portion of the urea, 200 grams), all Trolamine (triethanolamine) and the zinc pyrithione (Degussa Manufacturing) were added, and mixed for 5 minutes. The second portion of the urea as a dry solid having a mean particle size of about 450 microns was milled to a mean particle size of about 75 microns, prior to its addition to the mixture.

The mixture was then transferred rapidly (on the order of about 5 to 10 minutes) to a colloid mill, and processed cold (about 18 to 19° C.) for a period of about 5 minutes at a colloid mill gap setting that provides a mean distribution in the range of about 70 to about 120 microns. The viscosity of such a cream product may be 70000 centipoise (measured at 25° C.) and above.

Example 2

50 wt-% Urea Gel

| Ingredients | Mass (gms) | Wt-% |
|---|---|---|
| 1) Purified water | 192 | 19.20% |
| 2) Edetate disodium | 1 | 0.10% |
| 3) Urea | 503 | 50.30% |
| 4) Hydroxyethyl cellulose | 3 | 0.30% |
| 5) PEG-6 | 50 | 5.00% |
| 6) Xanthan gum | 3 | 0.30% |
| 7) Propylene glycol | 200 | 20.00% |
| 8) Zinc pyrithione | 1 | 0.10% |
| 9) Lactic acid | 20 | 2.00% |
| 10) Trolamine | 27 | 2.70% |
| Sum = | 1000 | 100.00% |

To prepare the aqueous phase, the purified water was added to a reactor at 20° C., then the edetate disodium was added, followed by 190 grams of urea (first portion of urea). Mixing continued for 10 minutes, then the hydroxyethylcellulose was added, and mixed for 30 minutes. Suitable mixers for the aqueous phase include, but are not limited to, a high shear mixer and a side sweep mixer.

To prepare the organic phase, the polyethylene glycol (PEG-6), xanthan gum, propylene glycol, and lactic acid were mixed together for 10 minutes to ensure appropriate swelling of the gum. The organic phase was added to the aqueous phase, and mixed in a homogenizer for 10 minutes. Then the second portion of urea (313 grams), zinc pyrithione and Trolamine (triethanolamine) were added. The mixture was discharged from the homogenizer, and processed through the colloid mill for five minutes at a colloid mill gap setting that provides a mean distribution in the range of about 70 to about 120 microns. The viscosity of such a gel product may be in the range of about 10000 to about 20000 centipoise (measured at 25° C.).

The gel product of the present invention is preferably free from glycerin. In alternate embodiments of the present invention, glycerin is used in lieu of propylene glycol. In yet other embodiments of the present invention, a combination of propylene glycol and glycerin are used. In still other embodiments of the present invention, polyethylene glycol (PEG) is substituted for the propylene glycol.

Example 3

35 wt-% Urea Lotion

| Ingredients | Mass (gms) | Wt-% |
|---|---|---|
| 1) Purified water | 468.2 | 46.82% |
| 2) Edetate disodium | 1 | 0.10% |
| 3) Cosmedia SPL | 3 | 0.30% |
| 4) Hydroxyethylcellulose | 1.5 | 0.15% |
| 5) Carbomer 940 | 1.8 | 0.18% |
| 6) Urea | 352 | 35.20% |
| 7) Xanthan gum | 1.5 | 0.15% |
| 8) Caprylic triglycerides | 50 | 5.00% |
| 9) Ceramides | 1 | 0.10% |
| 10) Linoleic acid | 7.5 | 0.75% |
| 11) Cholesterol | 8 | 0.80% |
| 12) Span 60 | 7.5 | 0.75% |
| 13) Tween 60 | 15 | 1.50% |
| 14) Cetyl alcohol | 11 | 1.10% |
| 15) Vitamin E | 30 | 3.00% |
| 16) Trolamine | 20 | 2.00% |
| 17) Lactic acid | 20 | 2.00% |
| 18) Zinc pyrithione | 1 | 0.10% |
| Sum = | 1000 | 100.00% |

To prepare the aqueous phase, the purified water was added to a water jacketed reactor preheated to 70° C. The edetate disodium was then added. Mixing continued for 10 minutes after addition of the edetate disodium. The Carbomer 940 was added, and mixed for 10 minutes. All of the urea was then added, followed by the xanthan gum. Mixing was continued for 30 minutes.

To prepare the organic phase, ingredients 8) through 15) and 17) were added in a second container. The mixture was heated to 70° C., and mixed occasionally to homogenize the components. Once visually homogenous, the organic phase was added to the aqueous phase, and mixing continued for 15 minutes. After this mixing time, the temperature was ramped (cooled) to 20° C. over the course of one hour. The Trolamine (triethanolamine) and zinc pyrithione were added after the cooling, and mixing continued for five minutes. The viscosity of such a lotion product may be 15000 to 30000 centipoise (measured at 25° C.).

One of the problems overcome by the inventive lotion formulation of Example 3 above is the viscosity breakdown that occurred through the use of lactic acid in combination with, for example, Trolamine and the carbomer. The weight percent of the components in the formulation, in particular the weight percent for the thickeners such as xanthan gum, were optimized to overcome the viscosity breakdown to provide a product of acceptable viscosity that contains urea and lactic acid. One aspect of the present invention is a product which comprises about 35 wt-% urea, about 2.0 wt-% lactic acid, and thickeners sufficient to achieve a viscosity in the range of about 15000 to about 30000 centipoise at 25° C.

The viscosity breakdown observed in developing the lotion formulation of Example 3 was also observed in developing the cream formulation of Example 1. In the Example 1 formulation as well, the weight percent of the components were optimized to overcome the viscosity breakdown to provide a product of acceptable viscosity that contains urea and lactic acid. One aspect of the present invention is a product with comprise about 50 wt-% urea, about 2.0 wt-% lactic acid, and thickeners sufficient to achieve a viscosity of about 70000 centipoise at 25° C.

Example 4

50 wt-% All Organic Formulation

In another embodiment of the present invention, an all organic formulation is provided that is waterless (free from water). In such an embodiment, all of the urea is suspended in the formulation because no water or other component is present in which to dissolve the urea. Thus, the all-organic formulations of the present invention avoid the problem of urea crystallization encountered with dissolved urea. In one embodiment, 50 wt-% urea, milled to a mean particle size less than about 150 microns, is added to suitable organic components, such as, for example, glycerin, and mixed. In another embodiment, a 50 wt-% urea cream includes the components substantially as shown above in Example 1, with glycerol or glycols in place of the water. In yet another embodiment, a 50 wt-% urea gel includes the components substantially as shown above in Example 2, with glycerol or glycols in place of the water. Glycerol or glycols with chain lengths less than C25 will be liquid at room temperature.

Example 5

Formulations with Crystal Inhibitors

As used herein and known to one skilled in the art, "crystal inhibitors" refer to molecules that inhibit crystallization. As noted above, needles are a common crystalline form, and one of the problems encountered with formulations having a concentration of urea greater than about 50 wt-% is the precipitation of urea in the form of needles. An alternative way of preventing or minimizing the formation of such needles, is to include one or more crystal inhibitors in the formulation. Suitable crystal inhibitors would include those molecules that would inhibit the crystallization, or precipitation in the form of needles, of the urea. Suitable crystal inhibitors include castor oil ethoxylates (a group of molecules with both hydrophobic and hydrophilic properties), xanthan gum, C8-C12 branched or linear alcohols, and cetyl alcohol. In another embodiment of the present invention, a 50 wt-% urea formulation is provided that comprises one or more crystal inhibitors. In another embodiment, a 50 wt-% urea cream is provided that comprises urea, water, a lipid, an antioxidant, a trace metal compound, and a crystal inhibitor. In yet another embodiment, a 50 wt-% urea gel is provided that comprises urea, water, propylene glycol, a trace metal compound, and a crystal inhibitor.

CONCLUSION

While various embodiments of the present invention have been described above, it should be understood that they have been presented by way of example only, and not limitation. The present invention is not limited to the preparation of compositions having the percentages of urea illustrated above, nor is it limited to particular lipids, antioxidants, trace metal compounds, or excipients, nor is the present invention limited to a particular scale, batch size or particle size. The present invention is also not limited to treatment of the dermatological conditions noted above, and the compositions of the present invention could be used for treatment of other dermatological conditions. Thus, the breadth and scope of the present invention should not be limited by any of the above-described exemplary embodiments, but should be defined only in accordance with the following claims and their equivalents.

What is claimed is:

1. A dermatological composition comprising:
about 50.3 wt-% urea;
about 0.30 wt-% hydroxyethylcellulose;
about 0.30 wt-% xanthan gum;
about 20.00 wt-% propylene glycol;
about 0.10 wt-% zinc pyrithione;
about 2.00 wt-% lactic acid; and
about 2.70 wt-% triethanolamine.

2. A dermatological composition, comprising:
about 0.18 wt-% carbomer;
about 35.2 wt-% urea;
about 5 wt-% caprylic triglyceride;
about 0.1 wt-% ceramide;
about 0.75 wt-% linoleic acid;
about 0.8 wt-% cholesterol;
about 3 wt-% vitamin E;
about 2 wt-% triethanolamine;
about 2 wt-% lactic acid; and
about 0.1 wt-% zinc pyrithione.

3. A dermatological composition, comprising:
about 50 wt-% urea;
about 5 wt-% caprylic triglyceride;
about 0.75 wt-% linoleic acid;
about 3 wt-% vitamin E;
about 2 wt-% lactic acid; and
about 0.1 wt-% zinc pyrithione.

* * * * *